Figure 1:
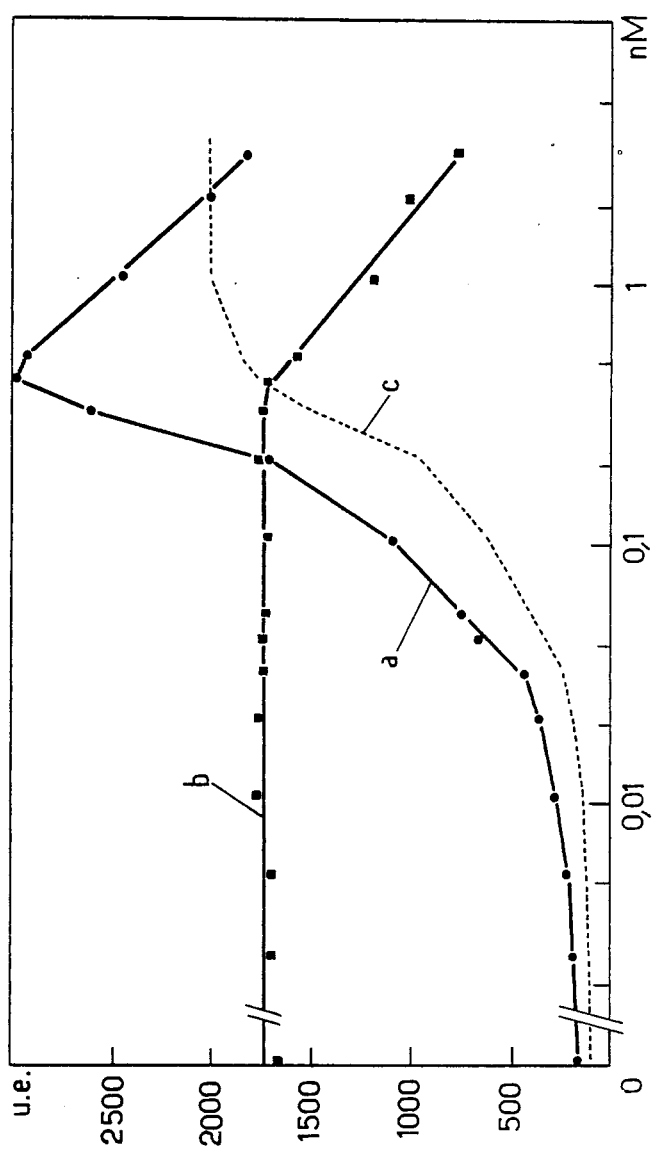

| United States Patent [19] | [11] Patent Number: 4,849,335 |
| Hofnung et al. | [45] Date of Patent: Jul. 18, 1989 |

[54] METHOD FOR DETECTING THE MUTAGENICITY OF SUBSTANCES SUSCEPTIBLE OF INDUCING THE DETERIORATION OF CELLULAR DNA, UTILIZING THE PRODUCTION OF AN SOS RESPONSE

[75] Inventors: Maurice Hofnung; Philippe Quillardet; David Perrin; Olivier Huisman; Richard D'Ari, all of Paris, France

[73] Assignee: Institut Pasteur, Paris, France

[21] Appl. No.: 614,446

[22] Filed: May 25, 1984

[30] Foreign Application Priority Data

Sep. 28, 1982 [FR] France ................... 82 16316

[51] Int. Cl.$^4$ .................. C12Q 1/68; C12Q 1/34; C12Q 1/42; C12Q 1/02
[52] U.S. Cl. .................................. 435/6; 435/18; 435/21; 435/29; 435/172.1; 435/849; 435/252.33; 935/82
[58] Field of Search .............. 935/29, 82, 59, 47, 935/14, 73, 40; 435/172.1, 849, 4, 6, 18, 21, 253, 172.3, 25, 29

[56] References Cited

FOREIGN PATENT DOCUMENTS 0063522 10/1982 European Pat. Off.

OTHER PUBLICATIONS

Quillardet et al., "Biochimie", vol. 64 (1982), pp. 797–801.
Quillardet et al, *Proc. Natl. Acad. Sci.*, vol. 79, pp. 5971–5975 (Oct. 1982) [not prior art].
Huisman and Ari, *Nature*, vol. 290, pp. 797–799 (Apr. 30, 1981).

*Primary Examiner*—Robert J. Warden
*Assistant Examiner*—Randall E. Deck
*Attorney, Agent, or Firm*—Oblon, Fisher, Spivak, McClelland & Maier

[57] ABSTRACT

A method for the detection of the mutagen effect of a substance or composition by producing culture of a micro-organism harboring a recombinant of a sfi gene and of a gene coding for a dosable enzyme in the presence of said substance or composition and measuring the activity of the dosable enzyme induced under the control of the sfi gene. When the latter is activated due to the mutagen character of said substance or composition, measuring the activity of a distinct enzyme synthesized by the microorganism and coded by a gene not involved in the activation process of the sfi gene and measuring the variation of the ratio of the activity of the abovesaid dosable enzyme to the activity of said distinct enzyme. Then comparing the variation that of the ratio of the activities of the same enzyme in a culture of the same microorganism, but in the absence of the mutagen substance.

12 Claims, 2 Drawing Sheets

METHOD FOR DETECTING THE MUTAGENICITY OF SUBSTANCES SUSCEPTIBLE OF INDUCING THE DETERIORATION OF CELLULAR DNA, UTILIZING THE PRODUCTION OF AN SOS RESPONSE

The invention relates to a method for detecting the mutagenicity of substances susceptible of inducing the deterioration of cellular DNA, utilizing the production of an SOS response. More particularly, it consists of an improvement of the method of detecting the possibly mutagenic character of substances, which forms the subject of European patent no. 82 400664. This method consists of cultivating in a suitable medium a micro-organism transformed by a recombinant of an sfi gene, particularly sfiA, and a gene coding for a measurable enzyme, advantageously β-galactosidase, in the presence of the substance being tested, the mutagen character of the latter being evaluated by the detection of a possible increase in the dosable enzyme, or in the hybrid enzyme, constituted at least in part by said dosable enzyme.

It has however been observed that the responses obtainable on the occasion of the employment of the method of detection described in the European patent application were modifiable, at least for certain concentrations of the substance under test, for example, when the latter is established to exert separate, independent actions, on the micro-organism under test, for example, when it possesses the property of inducing inhibition of the synthesis of proteins. In such a case, the induction of β-galactosidase or of the hybrid enzyme containing β-galactosidase may be sufficiently reduced, even when the substance under test possesses in fact mutagenic properties, to make aleatory the conclusions which can be drawn from the results obtained, at least as regards the effective intensity of the mutagenic properties of the substance under test.

It is an object of the invention to overcome this type of difficulty, more particularly to obviate possible disturbances due to properties often unknown of the substance under test and being added to its effectively mutagenic or genotoxic properties, and consequently providing a remedy for the possible masking of the induction of the dosable enzyme, by said disturbances.

The method of this invention, which utilizes an SOS reponse for detecting mutagenicity of a substance that can damage cellular DNA, comprises the steps of:

(a) incubating a microorganism in: (i) a first aliquot of a culture medium having a first concentration of said substance and (ii) a second aliquot of said culture medium having a second concentration of said substance; said second concentration being greater than said first concentration; said microorganism being a transformant containing an sfi gene and a second gene that codes for the synthesis of a measurable enzyme and that is placed under the control of said sfi gene; said microorganism also containing a third gene coding for the synthesis of a reference enzyme; said third gene for said reference enzyme not being involved in an activation process of said sfi gene producing an SOS response;

(b) measuring the activity of said measurable enzyme synthesized by said microorganism in said first and second aliquots during said incubating step (a);

(c) measuring the activity of said reference enzyme synthesized by said microorganism in said first and second aliquots during said incubating step (a);

(d) determining a first ratio of: (i) the activity of said measurable enzyme measured in step (b) in said first aliquot to (ii) the activity of said reference enzyme measured in step (c) in said first aliquot;

(e) determining a second ratio of: (i) the activity of said measurable enzyme measured in step (b) in said second aliquot to (ii) the activity of said reference enzyme measured in step (c) in said second aliquot; and (f) comparing said first and second ratios from steps (d) and (e); that said second ratio is greater than said first ratio indicating that said substance is mutagenic.

Preferably in the method of this invention: said second gene (coding for said measurable enzyme) and said sfi gene are an sfiA::operon lacZ recombinant; said microorganism is an *Escherichia coli;* and said first concentration of said substance in said culture medium in said first aliquot is zero.

Preferably, the other enzyme is selected from among those that the micro-organism hosting the abovesaid recombinant is capable of producing in significant amounts. As necessary, it is made constitutive in respect of the synthesis of the selected enzyme. This enzyme is advantageously constituted by alkaline phosphatase.

Of course, any other enzyme than alkaline phosphatase may be used as a reference. By way of example of an enzyme employable instead and in place of the alkaline phosphatase, will be mentioned: tryptophanase and glucuronidase. This is also valid as regards the abovesaid dosable enzyme, which may possibly consist of the enzyme coded by one of the following genes: UVR A, $rec^a$ or umuC.

The use of the abovesaid ratio as a parameter to be taken into consideration, renders the diagnosis essentially independent of the disturbances to which the synthesis of the dosable enzyme may be subject, in response to the induction of the sfi gene, as a consequence of the different properties of the substance under test and capable of influencing the enzymatic syntheses. It has in fact been observed that the disturbances concerned are always exerted so that, with respect both to the dosable enzyme induced and the reference enzyme, that the abovesaid ratio tends in any case to increase very notably, when the substance under test shows in fact a mutagen character, whatever the relative degrees of inhibition of the syntheses of the dosable enzyme, then induced by the activation of the sfi gene and of the reference enzyme.

The invention relates also more particularly to the strains of micro-organisms hosting the abovesaid recombinants, to the extent that they have been rendered constitutive as regards the synthesis of the reference enzyme. In this respect, the invention relates in particular to the strains of micro-organisms, more particularly E. coli, hosting the sfiA :: operon lacZ recombinant and enabling the expression of the lacZ gene, as a result of the activation of the sfiA gene, these micro-organisms being more particularly characterized in that they are also constitutive for the synthesis of the alkaline phosphatase.

A micro-organism hosting an sfi :: operon lac recombinant constitutive for the synthesis of the alkaline phosphatase may be obtained by the induction of a mutation in the phoR regulation gene or by transduction of the phoR marker by means of the bacteriophage P₁.

Figure 2:
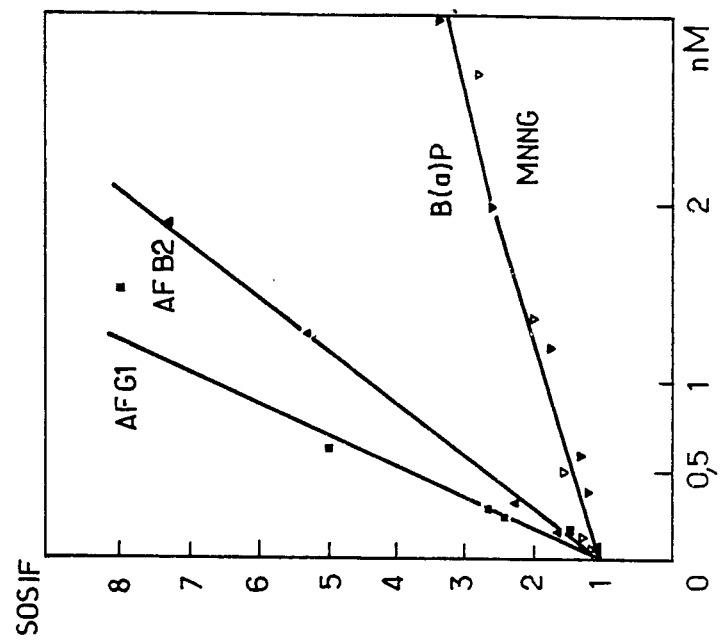
Figure 3:
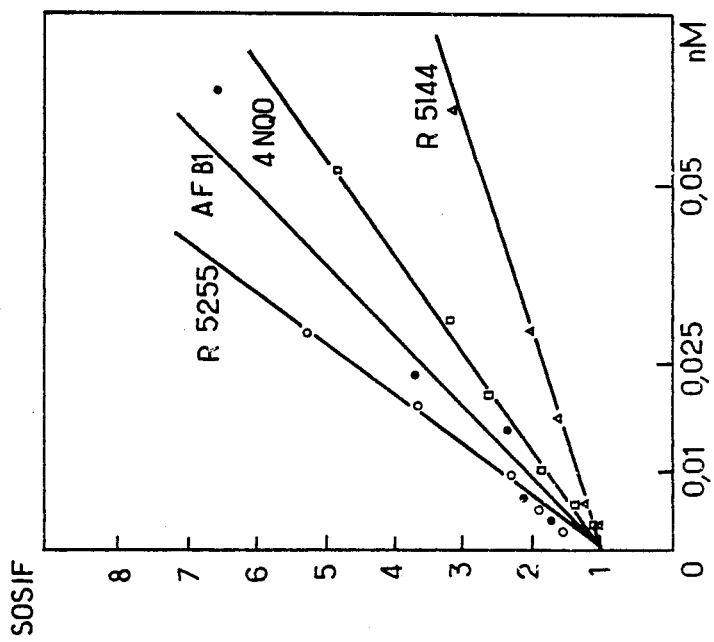

Other features of the invention will appear also in the course of the description of preferred embodiments of the method according to the invention, by employing a strain also in accordance with the invention, hosting an sfi::lac recombinant, and made constitutive for the synthesis of the alkaline phosphatase. Reference will be made to the drawing, in which:

FIG. 1 contains curves showing the variations in the activities (in enzymatic units: e.u.) of the β-galoactosidase and of the alkaline phosphatase respectively, on the one hand, and of the ratio of the β-galoactosidase activity to the alkaline phosphatase activity, on the other hand, as a function of the content (in nanomoles:nM of the culture medium of the abovesaid microorganism) in a well known carcinogenic (or genotoxic) compound, constituted by 4-nitroquinoline-1-oxide (4NQ0), FIGS. 2 and 3 contain the curves representing the variations of the logarithm of the abovesaid ratio, named below SOSIF (abbreviation of "SOS induction factor"), measurable in similar cultures, in the presence of different genotoxic substances, according to their respective concentrations in the culture media, in nanomoles per specimen tested.

The micro-organism employed in the tests whose description follows is a transformed *E. coli* strain, named PQ37, deposited in the National Collection of Culture Micro-Organisms (C.N.C.M.) of the Pasteur Institute of Paris, under no. I-205 on the date of Sept. 24, 1982. The genetic characteristics of this microorganism are as follows: F⁻ thr leu his-4 pyrD thi galE galK or T lacΔUI69 srl 300::Tn10 rpoB rpsL uvrA rfa trp::Muc+sfiA::Mud(AP, lac)c-Ts. It is constitutive for the synthesis of the alkaline phosphatase (Phoᶜ).

This strain has been obtained by genetic recombinations suitable to confer on it the above-indicated genotype, from the strain containing the recombinant sfiA::lacZ deposited at the C.N.C.M., under no. I-152 Apr. 13, 1981.

The method according to the invention can particularly be employed under the following conditions:

A culture of the abovesaid micro-organism previously developed up to the exponential phase in LB culture medium (Bacto tryptone 10 g, Bacto yeast extract 5 g, NaCl 10 g, water Q.S.P. 1 l), also containing ampicillin, is diluted ten times either in fresh medium, or in the activation mixture described by AMES B.N. and Coll. (1975), "Mutation Research" 31, 347–364. Aliquot parts of 0.6 ml are distributed in glass test tubes each containing a certain dose of the substance under test. After two hours incubation at 37° C. with shaking, the β-galoactosidase and alkaline phosphatase activities were determined.

It is possible in particular to carry out the determination of the alkaline phosphatase under the following condition: 2.7 ml of T buffer (solution of 121 g of Tris (hydroxy-methyl)-aminomethane per liter, whose pH has been adjusted to 8.8 with HCl) were added to 0.3 ml of the cell culture. The cell membranes were broken by the addition of an 0.1% sodium dodecyl-sulphate solution and 0.15 ml of chloroform and by vigorous shaking in a shaker of the VORTEX type. The tubes were then brought to the stabilized temperature of 28° C. The reaction starts by the addition of 0.6 ml of a paranitrophenylphosphate solution (PNPP) (4 mg/ml in T buffer). It is then stopped by the addition of 1 ml of 2 N HCl. 5 minutes later, 1 ml of 2 N Tris is added to restore the color, which is measured in the spectrophotometer at 420 nm. The enzyme units are calculated as for β-galoactosidase, by the method described by MILLER J. (1972) "Cold Spring Harbour laboratory", New York.

The determination of the β-galoactosidase activity is carried out by the method also described by MILLER. The operational procedure is the same as for the alkaline phosphatase, except that the T buffer is replaced by Z buffer whose composition is indicated below and that instead of the PNPP there is used the substrate constituted by (ONPG) and finally the reaction is interrupted with sodium carbonate.

The composition of the Z buffer is as follows (per liter):

Na₂ HPO₄, 7H₂O: 16.1 g
NaH₂PO₄, H₂O: 5.5 g
KCl: 0.75 g
MgSO₄, 7 H₂O: 0.25 g
βmercaptoethanol, pH adjusted to 7.0: 2.7 ml pH adjusted to 7.0.

The curves of FIG. 1 are representative of the variations, as a function of the concentrations of the genotoxic substance (4NQO):
of the β-galoactosidase activity (curve a);
of the alkaline phosphatase activity (curve b);
of the SOSIF ratio (curve c).

The various measurements were carried out 2 hours after the start of the experiment. In fact, experience shows that the curve representing the SOSIF factor, for any concentration of genotoxic substance, reaches a plateau after 70 to 100 minutes, and remains stable generally for more than 2 hours. The curves show in addition, that beyond a certain concentration of genotoxic substance, there follows an inhibiting effect of the synthesis of the proteins manifested by a reduction in the β-galoactosidase and alkaline phosphatase activities. However, the SOSIF ratio, used for evaluating the mutagenic or genotoxic effect of the substance under test, is practically unaffected. In fact, it remains substantially constant at concentrations of the genotoxic substance which are of a nature to inhibit the synthesis of the proteins.

The curves of FIGS. 2 and 3 represent variations in the SOSIF ratio as a function of the concentrations used of various genotoxic agents.

The genotoxic substances used were as follows:
R 5255 : 2-nitro-5-methoxybenzofuran
AF B1 : aflatoxin
4NQO : 4-nitroquinoline-1-oxide
R 5144 : 2-nitro-benzofuran
AF G1 : aflatoxin G
AF B2 : aflatoxin B
B(a)P : benxo-a-pyrene
MNNG : N-methyl-N'-nitro-N-nitrosoguanidine It is particularly remarkable that the SOSIF factor is a substantially linear function of the concentration of the genotoxic substance used, in particular for doses contained within a range of relatively low doses. The sensitivity of the test is particularly remarkable, if it is observed that variations of the measured values extend over a range of 1 to 60 million, in passing from the lower limit to the upper limit of the range of concentrations expressed as abscissae.

Consequently the invention provides a test of a quite remarkable sensitivity, suitable for giving accurate quantitative indications, having regard to the intensity of the mutagen effect of the tested substances.

As is self-evident and as results besides already from the foregoing, the invention is in no way limited to those of its types of application and embodiments which have been more especially envisaged; it encompasses on the contrary all modifications.

We claim:

1. A method, utilizing an SOS response for detecting mutagenicity of a substance that can damage cellular DNA; said method comprising the steps of:
   (a) incubating a microorganism in: (i) a first aliquot of culture medium having a first concentration of said substance and (ii) a second aliquot of said culture medium having a second concentration of said substance; said second concentration being greater than said first concentration; said microorganism being a transformant containing an sfi gene and a second gene that codes for the synthesis of a measurable enzyme and that is placed under the control of said sfi gene; said microorganism also containing a third gene coding for the synthesis of a reference enzyme; said third gene for said reference enzyme not being involved in an activation process of said sfi gene producing an SOS response;
   (b) measuring the activity of said measurable enzyme synthesized by said microorganism in said first and second aliquots during said incubating step (a);
   (c) measuring the activity of said reference enzyme synthesized by said microorganism in said first and second aliquots during said incubating step (a);
   (d) determining a first ratio of: (i) the activity of said measurable enzyme measured in step (b) in said first aliquot to (ii) the activity of said reference enzyme measured in step c) in said first aliquot;
   (e) determining a second ratio of: (i) the activity of said measurable enzyme measured in step (b) in said second aliquot to (ii) the activity of said reference enzyme measured in step (c) in said second aliquot; and
   (f) comparing said first and second ratios from steps (d) and (e); that said second ratio is greater than said first ratio indicating that said substance is mutagenic.

2. The method of claim 1, wherein said second gene, coding for said measurable enzyme, is a lacZ, UVR A, $rec^a$ or umuC gene.

3. The method of claim 1, wherein said sfi gene is an sfiA gene.

4. The method of claim 1, wherein said second gene, coding for said measurable enzyme, and said sfi gene are an sfiA::operon lacZ recombinant.

5. The method of claim 4, wherein said measurable enzyme is $\beta$-galactosidase and said reference enzyme is alkaline phosphatase.

6. The method of claim 1, wherein said reference enzyme is alkaline phosphatase, tryptophanase or glucuronidase.

7. The method of claim 6, wherein said microorganism is constitutive for the synthesis of said reference enzyme.

8. The method of claim 1, wherein said microorganism is an *Escherichia coli*.

9. The method of claim 1, wherein said microorganism is in an exponential phase during said incubating step (a).

10. The method of claim 1, wherein said first concentration of said substance in said culture medium in said first aliquot is zero.

11. A microorganism hosting an sfiA::operon lacZ recombinant and expressing the lacZ gene following activation of the sfiA gene; said microorganism also being constitutive for the synthesis of alkaline phosphotase.

12. The microorganism of claim 11 which is an *E. coli* in an exponential phase.

* * * * *